United States Patent [19]

Moussavi et al.

[11] Patent Number: 4,996,311

[45] Date of Patent: Feb. 26, 1991

[54] OCTASUBSTITUTED LITHIUM PHTHALOCYANINES, THEIR METHOD OF PREPARATION AND THEIR USE IN EPR (ELECTRONIC PARAMAGNETIC RESONANCE) MAGNETOMETRY

[75] Inventors: Mehdi Moussavi; Liliane Secourgeon, both of Saint Egreve, France

[73] Assignee: Commissariat A. L'Energie Atomique, Paris France

[21] Appl. No.: 379,980

[22] Filed: Jul. 14, 1989

[30] Foreign Application Priority Data

Jul. 20, 1988 [FR] France ................................ 88 09831

[51] Int. Cl.$^5$ ............................................. C09B 47/04
[52] U.S. Cl. ................................ 540/139; 204/59 QM
[58] Field of Search ........................................ 540/139

[56] References Cited

U.S. PATENT DOCUMENTS

3,615,558 10/1971 Webster et al. ...................... 540/139

FOREIGN PATENT DOCUMENTS

0188941 12/1985 European Pat. Off. .

OTHER PUBLICATIONS

Cuellar et al., "Synthesis and Characterization . . . ", CA 95 179991k, (1981).
Van der Pol et al., "Evidence of an Ordered Columan . . . ", CA 110 126124b, (1989).
Chemical Abstracts, Vol. 95, 1981, No. 179991k.
Journal of the Chemical Society, Chem. Commun., 1983, pp. 962-963.

*Primary Examiner*—Alan L. Rotman
*Assistant Examiner*—Celia Chang
*Attorney, Agent, or Firm*—Pearne, Gordon, McCoy & Granger

[57] ABSTRACT

The invention concerns an octasubstituted lithium phthalocyanine responding to the formula:

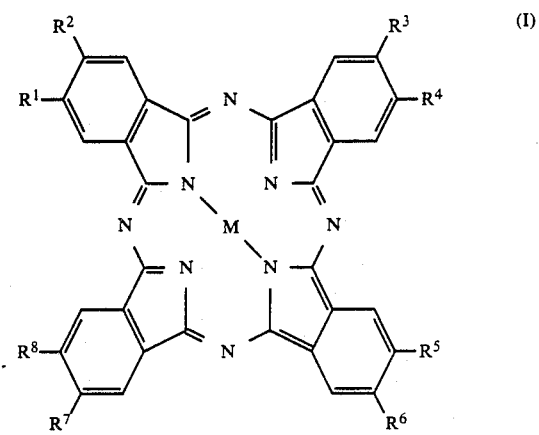

in which $R^1$, $R^2$, $R^3$, $R^4$, $R^5$, $R^6$, $R^7$ and $R^8$, which are identical or different, represent an alkyl or alcoxy radical, possibly substituted by fluorine, and M represents Li or $Li_2$.

When M represents Li, this involves a lithium phthalocyanine octasubstituted like a radical which can be used in electronic paramagnetic resonance magnetometry.

In this case, the substituents are preferably all identical and represent the methyl or methoxy radical.

6 Claims, 1 Drawing Sheet

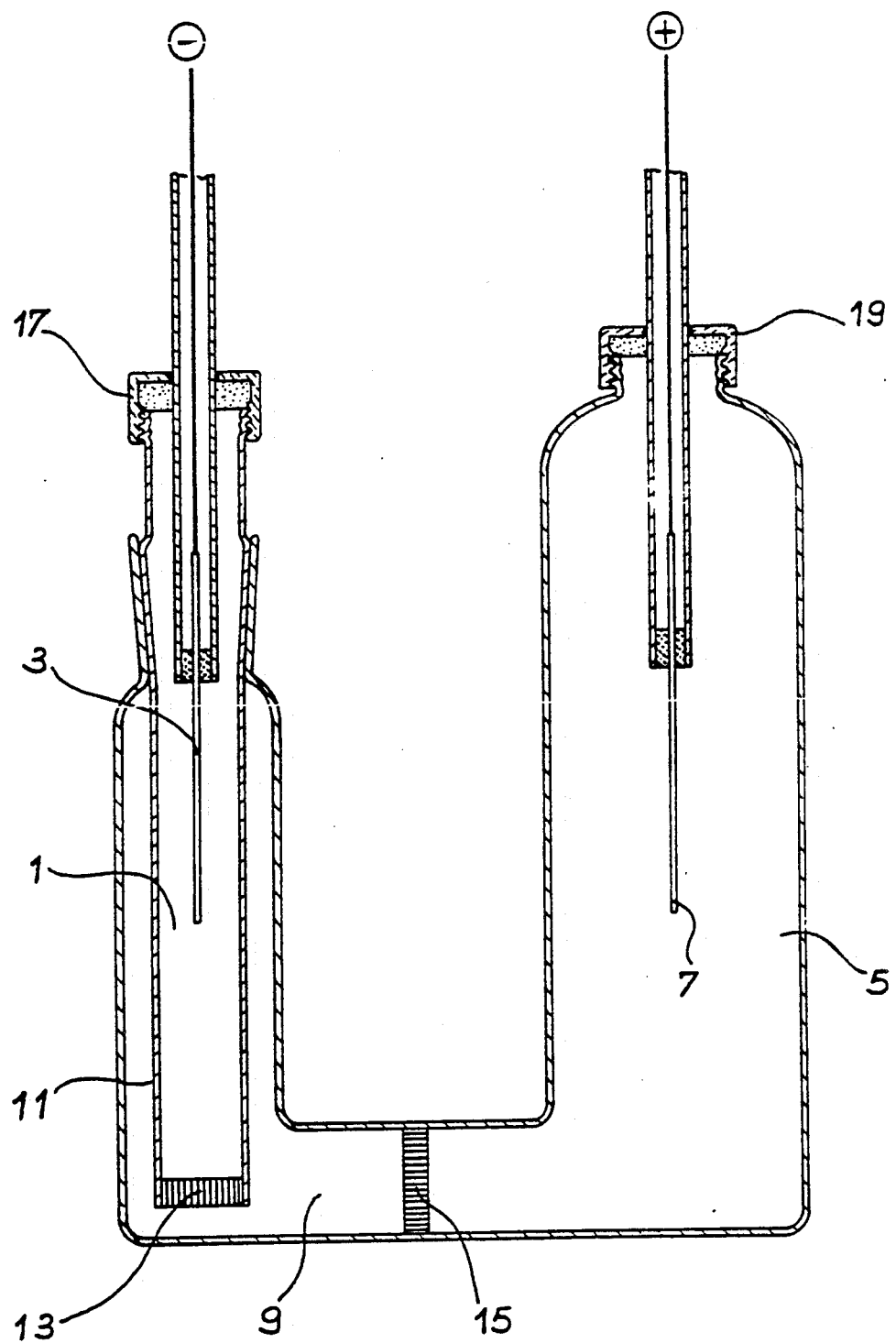

OCTASUBSTITUTED LITHIUM PHTHALOCYANINES, THEIR METHOD OF PREPARATION AND THEIR USE IN EPR (ELECTRONIC PARAMAGNETIC RESONANCE) MAGNETOMETRY

FIELD OF THE INVENTION

The present invention concerns new octasubstituted lithium phthalocyanines, in particular in the form of stable radical-like compounds able to be used to measure magnetic fields by electronic paramagnetic resonance (EPR).

BACKGROUND OF THE INVENTION

For a number of years, much research has been carried out to discover organic, metallic or semiconductive radicals able to be used in magnetometry (EPR) and in particular ionic systems have been developed, such as fluoranthene salts and tetrathiafulyalene-tetracyanoquinodimethane, described by E. Dormann et al in the Journal of Magnetism and Magnetic Materials, 54-57, (1986), p. 1315-1316.

The use of these magnetometry compounds suffers from certain drawbacks. In fact, the salts of radical ions belonging to the fluoranthene family or (TTF-CNQ) are systems with several compounds and the problems linked to their unpredictable stoichiometric qualities and lack of chemical and thermal stability are inevitable. In addition, the electric conduction properties of these substances disturb the magnetic field measurements via the skin effect.

Also, researches have been carried out so as to find other more high-performing materials.

Amongst the materials able to offer properties suitable for use in magnetometry, radical-like phthalocyanines, such as lithium phthalocyanine, have been considered, as described by Turek et al in the publication Solid State Communications, Vol. 63, n 8, p. 741-744, 1987. This radical-like lithium phthalocyanine may be prepared by potentiostatic electrochemical oxidation of dilithiated phthalocyanine, as described by Sujimoto et al in the publication J. Chem. Soc. Chem. Commun., 1986, p. 962-963.

The radical-like lithium phthalocyanine seemed suitable for carrying out magnetic measurements, but the signal obtained with this compound is inadequate to justify its industrial application. Moreover, the radical-like lithium phthalocyanine is extremely sensitive to the action of oxygen, as described by Turek et al in the aforesaid document, which leads to a widening of the EPR line.

Furthermore, the preparation of the radical-like lithium phthalocyanine by potentiostatic electrochemical oxidation does not make it possible to obtain crystals having satisfactory properties. In fact, the generation of lithium phthalocyanine crystals starts at a maximum intensity value in order to reduce subsequently. This results in a rapid non-reproducible growth of the radical-like lithium phthalocyanine in the form of a powder or very small crystals, which comprises defects in the best of cases.

SUMMARY OF THE INVENTION

The precise object of the present invention is to provide new lithium phthalocyanines able to be used in EPR magnetometry, said new lithium phthalocyanines mitigating the drawbacks of the radical-like lithium phthalocyanine described above.

According to the invention, the lithium phthalocyanine is an octasubstituted lithium phthalocyanine responding to the formula :

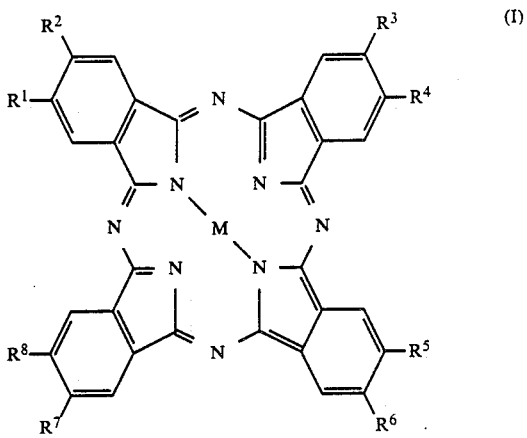

in which $R^1$, $R^2$, $R^3$, $R^4$, $R^5$, $R^6$, $R^7$ and $R^8$, which are identical or different, represent an alkyl or alkoxy radical with 1 to 3 carbon atoms, possibly substituted by one or more fluorine atoms, and M represents Li or $Li_2$.

When M represents $Li_2$, this involves the dilithiated precursor of the radical-like octasubstituted lithium phthalocyanines of the invention.

When M represents Li, this involves the radical-like octasubstituted lithium phthalocyanine able to be used to EPR magnetometry.

The presence on this radical-like lithium phthalocyanine of the substituents $R^1$ to $R^8$ makes it possible to improve the properties of the phthalocyanine for its use in EPR magnetometry and to facilitate its preparation from the dilithiated precursor.

In fact, the EPR signal of the non-substituted radical-like lithium phthalocyanine is widened by the presence of oxygen, as seen previously. Also, this compound can only be used in magnetometry under a vacuum. However, irrespective of the vacuum level of the conditioning of a sample of a radical-like lithium phthalocyanine, the residual oxygen remains in the inclusion sites existing in the radical-like PcLi crystals.

According to the invention, this drawback is overcome by substituting the phthalocyanine at the periphery by groupings of adequate nature and size making it possible to fill up the space between the molecules so as to render more compact the crystalline structure and prevent oxygen from entering. The substituents are electron donor groupings which moreover have a favorable effect on the oxidation reaction of the dilithiated precursor in the method for preparing the radical-like octasubstituted lithium phthalocyanine by electrochemical oxidation of the dilithiated precursor.

The substituents making it possible to obtain this effect are electron donor groupings which must not have a significant donor effect which would be expressed by a deterioration of the stability of the radical-like lithium phthalocyanine. The donor electron effect ought to no longer be insufficient since this would not be translated by a significant improvement of the properties of the radical-like lithium phthalocyanine. The donor effect may be controlled by the substitution of one or more hydrogen atoms by the corresponding number of fluorine atoms on 2 to 8 carbon atoms of the octamethoxy phthalocyanine, or more in the case where, as regards the phthalocyanine in question, the substitutino grouping comprises several carbon atoms.

According to the invention, the substituents are alkyl or alkoxy radicals having from 1 to 3 carbon atoms. In these radicals, one or more hydrogen atoms may be replaced by one or more fluorine atoms so as to adjust the overall donor effect of these substituents on the phthalocyanine.

Generally speaking, $R^1$ to $R^8$ represent identical radicals, preferably having a carbon atom threshold, such as methoxy, methyl and trifluoromethoxy radicals.

The methoxy radical is preferably used as this involves an electron mesomeric donor which activates the phthalocyanine macrocycle and facilitates the loss of an electron by the dilithiated precursor.

In fact, it has been established that by using as a substituent an attracting grouping, such as fluorine, the macrocycle is strongly deactivated by rendering oxidation of the dilithiated precursor extremely difficult.

The dilithiated precursors of the radical-like lithium phthalocyanines of the invention may be prepared by conventional methods from a disubstituted derivative or from one or more disubstituted benzene derivatives responding to the formula :

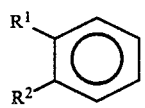 (II)

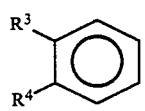 (III)

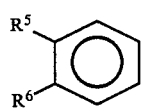 (IV)

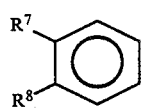 (V)

in which $R^1$, $R^2$, $R^3$, $R^4$, $R^5$, $R^6$, $R^7$, and $R^8$ have the significance given above.

For this preparation, these distributed derivatives are transformed into tetrasubstituted derivatives responding to the formulae:

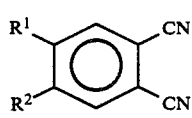 (VI)

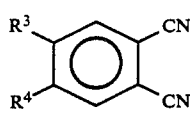 (VII)

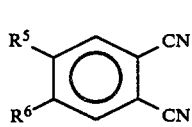 (VIII)

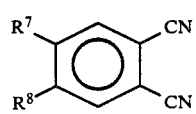 (IX)

one or more of these tetrasubstituted derivatives then being made to react with the lithium so as to form the corresponding octasubstituted $PcLi_2$.

In the case of each of the disubstituted derivatives of formulae II to V described above, the tetrasubstituted derivative is obtained by carrying out the following reactions:

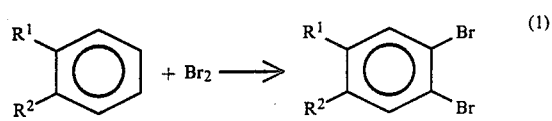 (1)

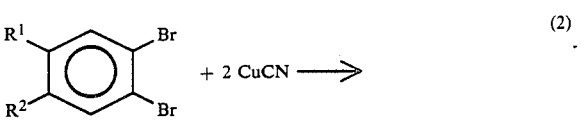 (2)

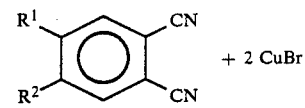

The first reaction (1), which consists of preparing the dibrominated derivative, may be effected by the action of the bromine in the presence of catalysts, such as powdered iron and iodine, as described by E. Klingsberg in Synthesis (1972), p. 29–30 in the case of the preparation of the dibromo orthoxylene derivative.

The reaction (2) may be effected by making the derivative obtained by the reaction 1 react with a slight excess diluted solution of copper cyanine using dimethylformamide as a solvent and by operating on the reflux.

The preparation of the octasubstituted dilithiated phthalocyanine may be carried out next by making one or more derivatives responding to the formulae VI to IX react with the lithium in an alcohol solution, such as amylic alcohol. When this reaction with 2, 3 or 4 different derivatives as mentioned above has been carried out, a mixture is obtained of octasubstituted dilithiated phthalocyanines, said mixture needing to be separated so as to isolate the molecules having identical formulae. This separation may be carried out by liquid chromatography on an aluminum or silica column.

Generally speaking, the process starts with a disubstituted benzene derivative threshold in which $R^1$ and $R^2$ may be identical or different. In this case, the dilithiated octasubstituted phthalocyanine is exclusively obtained with the formula :

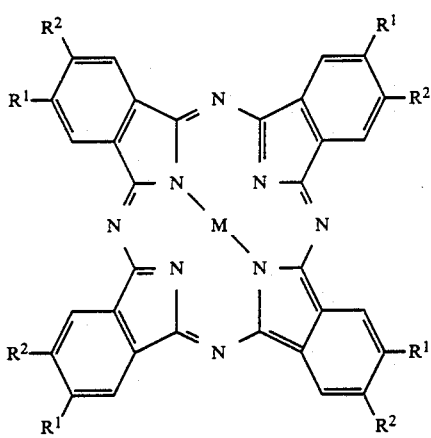

in which $R^1$ and $R^2$ have the significance given above and M represents $Li_2$.

According to the invention, one passes from the octasubstituted dilithiated derivative to the radical-like lithium phthalocyanine octasubstituted by electrochemical oxidation effected in conditions different from those used previously to pass from the dilithiated phthalocyanine to the radical-like lithium phthalocyanine.

Also, the object of the invention is to provide a method for preparing octasubstituted radical-like lithium phthalocyanine, said method consisting of oxidizing an octasubstituted dilithiated phthalocyanine with the formula:

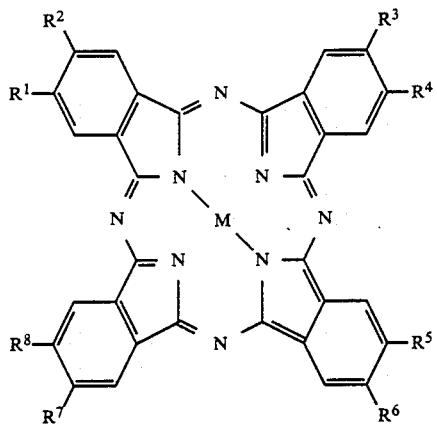

In which $R^1$, $R^2$, $R^3$, $R^4$, $R^5$, $R^6$, $R^7$ and $R^8$ have the significance given above and M represents $Li_2$ by galvanostatic monoelectronic oxidation.

In this method, a weak current is applied at the start of the oxidation reaction so as to slow down the formation of nucleus crystals; thus, the speed of crystal growth and accordingly the crystalline quality of the product obtained is better controlled.

In fact, the peripheral substitution of the phthalocyanine results in a displacement in the cathodic direction of the oxidation-reduction potentials, in other words the compounds octasubstituted by the alkyl or alkoxy radicals are oxidized more easily than the non-substituted phthalocyanine. However, it would be proper to limit the number of carbons of the substituent groups to 3 so as to prevent the final synthesis stage of becoming uncontrollable:

When according to the prior Art the electrochemical oxidation of the dilithiated derivative is carried out according to the potentiostatic method, a potential is imposed on the terminals of the electrodes immersed in a solution of dilithiated phthalocyanine, said potential corresponding to that of the range of the intensity variations curve of the current i according to the potential. In this way, the generation of the radical-like lithium phthalocyanine crystals would start at a maximum intensity value so as to subsequently reduce. Thus, a rapid non-reproducible growth of the radical-like lithium phthalocyanine would be obtained in the form of a powder or very small crystals comprising defects.

BRIEF DESCRIPTION OF THE DRAWINGS

The invention shall be more readily understood from a reading of the following description, given by way of illustration and being in no way restrictive, accompanied by the annexed drawing which represents a three-compartment electrochemical cell for implementing the method of the invention.

BRIEF DESCRIPTION OF THE PREFERRED EMBODIMENTS

This figure (1) shows that the electrochemical cell includes a first cathodic compartment (1) connected to a cathode (3), a second anodic compartment (5) connected to an anode (7) and an intermediate compartment (9) situated between the cathodic compartment and the anodic compartment. The cathodic compartment is delimited by a glass casing (11) provided at its lower part with a porous sintered glass pellet (13).

The anodic compartment (5) is closed at its lower part by a porous sintered glass pellet (15) and the intermediate compartment (9) is delimited in the cell between the porous sintered glass pellets (13 and 15). The anodic and cathodic compartments may be sealed off at their upper part by sealing stoppers (17 and 19).

The electrodes (3 and 7) may be connected to a d.c. current generator.

In order to carry out the electrochemical oxidation of the octasubstituted dilithiated phthalocyanine derivative, the latter is introduced into a solution of a solvent comprising a support electrolyte in the anodic compartment (5) of the cell. The cathodic compartment with the same solvent and the same support electrolyte is filled, then the two compartments are properly degassed and the cell is hermetically sealed. Then a potential difference is applied between the electrodes (3 and 7) so as to cause the weak currents to pass at the start of oxidation and the currents are then increased at specific moments so as to collect those crystals having the best quality.

The solvent used may be a ketone, such as butanone-2, and the support electrolyte may be a quaternary ammonium salt, such as tetrabutylammonium perchlorate.

The following examples for the preparation of radical-like lithium octamethoxyphthalocyanine and radical-like lithium octamethylphthalocyanine are given to illustrate the invention, said examples being in no way restrictive.

EXAMPLE 1

Preparation of radical-like lithium octamethoxy ohthalocyanine (a) Preparation of 1.2-dibromo-4.5-dimethoxybenzene from 1.2-dimethoxybenzene This reaction corresponds to the following diagram:

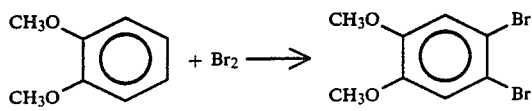

156 g (0.98 mols) of bromine is added over a period of five hours to 68 g (0.49 mols) of 1.2-dimethoxybenzene at a temperature of from 5° C. to 10° C. by using the powdered iron and iodine as catalysts at the rate of 1 g of iron and 1 iodine crystal.

Towards the end of adding bromine, the mixture is easily agitated by diluting it with dichloromethane which is then partially eliminated by distillation over a vapor bath. Then the product obtained is filtered and dried. The raw product is washed with cold methanol (4° C.) until the characteristic rufous color of the bromine is eliminated. Thus, 106 g of clear beige-colored 1.2-dibromo-4.5-dimethoxybenzene is obtained, which corresponds to a yield of 73%.

(b) Preparation of 1.2-dicyano-4.5 methoxy-benzene

This reaction corresponds to the following reactional diagram :

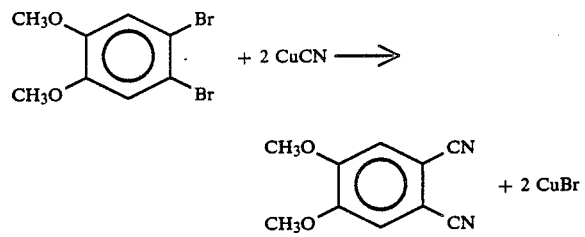

A mixture of 106 g (0.36 mols) of 1.2-dibromo-4.5-dimethoxy-benzene, 98 g (1.06 mols) of copper cyanide and 300 ml of dimethylformamide is brought to reflux for five hours, then the mixture is cooled and is poured into 500 ml of 30% ammonia. The residue is again mixed for 10 minutes, then is filtered and washed with water and dried. The product is extracted by ether for 24 hours by using a Soxhlet device and the solvent is evaporated. Thus, 40 g of 1.2-dicyano-4.5 dimethoxybenzene is obtained in the form of white flakes, which corresponds to a yield of 58%.

(c) Preparation of dilithiated octamethoxyphthalocyanine 38 g (0.2 mols) of 1.2-dicyano-4.5 dimethoxybenzene is added to a solution of 2 g of lithium in 150 cm3 of amylic alcohol. Then the mixture is heated, a highly exothermal reaction takes place and the dilithium octamethoxyphthalocyanine is deposited. The mixture is boiled for 90 minutes, then cooled and diluted with 0.5 liters of benzene and is then kept for three hours at 4° C. Then the mixture is filtered and 8 g of dilithium octamethoxyphthalocyanine is thus obtained which is extracted with acetone which has been firstly dried on sodium sulphate. By evaporation under reduced pressure, 5 g of dilithium octamethoxyphthalocyanine is obtained in the form of a crystalline deposit, which corresponds to a yield of 13%.

(d) Preparation of radical-like lithium octamethylphthalocyanine

For this preparation, the electrochemical cell represented on FIG. 1 is used to galvanostatically carry out monoelectronic oxidation of the dilithium octamethoxyphthalocyanine obtained previously. The electrochemical cell and the electrodes (3) and (7), both constituted by platinum wires with a diameter of 1 mm and a length of 3.5 mm, are firstly properly cleaned and are dried in an oven at 60° C. Then into the anodic compartment (5), a solution of 90 mg of $(CH_3O)_8$ $PcLi_2$ and 500 mg of tetrabutylammonium perchlorate (TBAP) is introduced into 100 ml of butanone-2. Then the cathodic compartment (1) is filled with 50 ml of butanone-2 containing 500 mg of TBAP. Then degassing is carried out by pure argon bubbling through in the two compartments, the cell being hermetically sealed with the stoppers (17) and (19). Then the following currents are applied to the terminals of the cell :

0.5μA for 15 hours,
2.5μA for 24 hours,
5μA for 72 hours, and
10μA for 24 hours.

Polycrystalline particles of radical-like lithium octamethoxyphthalocyanine formed at the anode are thus obtained. These polycrystalline particles are recovered and then the crystals remaining on the anode are collected by decantation after three successive washings with 100 ml portions of pure dry acetone. Thus in all, 20 mg of radical-like lithium octamethoxyphthalocyanine is obtained, which corresponds to a yield of 22.5%.

EXAMPLE 2

Preparation of radical-like lithium octamethyl phthalocyanine

The same mode of operation as in example 1 is used to prepare this phthalocyanine, except this preparation starts with 1.2-dimethylbenzene, namely 0-xylene.

The radical-like lithium phthalocyanine octamethyl is thus obtained with a yield similar to the one obtained in example 1.

The radical-like lithium octamethoxyphthalocyanine and radical-like lithium phthalocyanine octamethyl of examples 1 and 2 possess sound properties in order to be used in magnetometry, especially in a magnetometer, such as the one described in the French patent FR-A- 2 603 384.

In the attached table, the results obtained with various materials are entered and relate to the measurement of the maximum slope of the RPE signal at 1.8 MHz, namely the slope of the central part of the curve derived from the absorption spectrum of the material by using a low field RPE spectrometer. The values obtained make it possible to make quantitative comparisons of the materials for their possible use in magnetometry. It can be observed from this table that the radical-like octasubstituted lithium phthalocyanines of the invention are more high-performing than those of known materials. Furthermore, the $(CH_3O)_8PcLi$ or $(CH_3)_8PcLi$ EPR signal has a maximum slope over a wide range of excitation and detection fields, which implies that adjustment can clearly be easily made so as Lo obtain maximum performances when these materials are used in magnetometry.

In fact, the maximum slope for the signal of all fine EPR materials is observed for specific power, excitation and detection values.

This table also indicates the stability of the materials at 20° C. and indicates that the octasubstituted radical-like lithium phthalocyanines of the invention also possess sound stability.

TABLE

| Material | Max. slope of EPR signal at 1.8 MHz per mg | Stability (at 20° C.) |
| --- | --- | --- |
| 2.2-diphenyl-1-picrylhydrazyle | $0.1 \cdot 10^{-9}$ | very stable |
| Tetracyano quinodimethane diquinoline | $45 \cdot 10^{-9}$ | very stable |
| Fluoranthene hexafluorophosphate | $70 \cdot 10^{-9}$ | unstable |
| Naphthalene hexafluorophosphate | $90 \cdot 10^{-9}$ | highly unstable |
| PcLi | $40 \cdot 10^{-9}$ | very stable |
| $(CH_3O)_8$ PcLi | $100 \cdot 10^{-9}$ | very stable |
| $(CH_3O)_8$ PcLi | $90 \cdot 10^{-9}$ | very stable |

WHAT IS CLAIMED IS :

1. Octasubstituted lithium phthalocyanine corresponding to the formula :

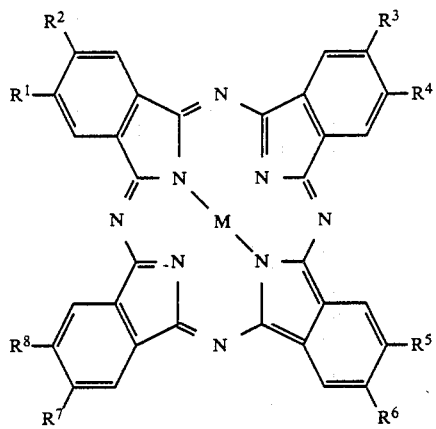

(I)

in which $R^1$, $R^2$, $R^3$, $R^4$, $R^5$, $R^6$, $R^7$ and $R^8$, which are identical or different, represent an alkoxy or alkyl radical having from 1 to 3 carbon atoms, optionally substituted by one or more fluorine atoms, and M represents Li.

2. Lithium phthalocyanine according to claim 1, wherein $R^1$ to $R^8$ are identical.

3. Lithium phthalocyanine according to claim 2, wherein $R^1$, $R^2$, $R^3$, $R^4$, $R^5$, $R^6$, $R^7$ and $R^8$ represent the methoxy radical.

4. Lithium phthalocyanine according to claim 2, wherein $R^1$, $R^2$, $R^3$, $R^4$, $R^5$, $R^6$, $R^7$ and $R^8$ represent the methyl radical.

5. Octasubstituted lithium phthalocyanine corresponding to the formula :

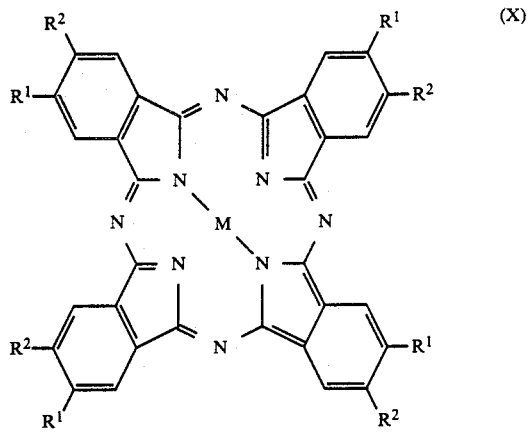

(X)

in which $R^1$ and $R^2$, which may be identical or different, represent an alkoxy or alkyl radical with from 1 to 3 carbon atoms, and M represents Li.

6. Octasubstituted lithium phthalocyanine according to claim 5, wherein $R^1$ and $R^2$, which are identical or different, represent the methoxy or methyl radical.

* * * * *